United States Patent
Höglund et al.

(10) Patent No.: US 6,298,845 B1
(45) Date of Patent: Oct. 9, 2001

(54) VAPORIZER

(75) Inventors: Kasper Höglund, Rönninge; Pär Emtell, Vällingby, both of (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/382,335

(22) Filed: Aug. 25, 1999

(30) Foreign Application Priority Data

Sep. 2, 1998 (SE) .................................................. 9802957

(51) Int. Cl.[7] .................................................. A61M 15/00
(52) U.S. Cl. .............................. 128/203.12; 128/203.14; 128/203.24; 128/203.25
(58) Field of Search .................. 128/203.12, 203.14, 128/203.24, 203.25

(56) References Cited

U.S. PATENT DOCUMENTS

| | | | | |
|---|---|---|---|---|
| 3,158,154 | * | 11/1964 | Schreiber ........................ | 128/203.25 |
| 3,588,057 | * | 6/1971 | Breiling ........................... | 128/203.25 |
| 3,593,710 | * | 7/1971 | Eichelman ....................... | 128/203.25 |
| 3,651,805 | * | 3/1972 | Breiling ........................... | 128/203.25 |
| 4,691,700 | | 9/1987 | Brychta et al. ................. | 128/200.21 |
| 4,770,168 | * | 9/1988 | Rusz et al. ...................... | 128/203.14 |
| 4,919,125 | * | 4/1990 | Heaton et al. .................. | 128/203.14 |
| 5,146,915 | * | 9/1992 | Montgomery ................... | 128/203.14 |
| 5,168,866 | | 12/1992 | Montgomery ................... | 128/203.12 |
| 5,197,462 | * | 3/1993 | Falb et al. ....................... | 128/203.14 |
| 5,235,971 | * | 8/1993 | Falb et al. ....................... | 128/203.14 |
| 5,243,973 | * | 9/1993 | Falb et al. ....................... | 128/203.25 |
| 5,335,652 | * | 8/1994 | Falb et al. ....................... | 128/203.25 |
| 5,390,665 | * | 2/1995 | Leach .............................. | 128/203.25 |
| 5,535,737 | * | 7/1996 | Galbenu .......................... | 128/203.14 |
| 5,546,931 | * | 8/1996 | Rusz ................................ | 128/203.14 |
| 5,636,626 | * | 6/1997 | Bloch et al. ..................... | 128/203.24 |
| 5,649,531 | * | 7/1997 | Heinonen ........................ | 128/203.12 |
| 5,664,561 | | 9/1997 | Kersey ............................ | 128/203.26 |
| 5,671,729 | * | 9/1997 | Moll et al. ....................... | 128/203.14 |

FOREIGN PATENT DOCUMENTS

| | | |
|---|---|---|
| 0 038 531 | 4/1981 | (EP) . |
| 0 454 390 | 10/1991 | (EP) . |
| 0 469 797 | 2/1992 | (EP) . |
| 0 545 567 | 6/1993 | (EP) . |
| 519203 | 3/1940 | (GB) . |
| 2 097 272 | 11/1982 | (GB) . |
| 2 252 913 | 8/1992 | (GB) . |

OTHER PUBLICATIONS

Halothane Vaporizer 950, Enflurane Vaporizer 951, Isoflurane Vaporizer 952 Operating Manual, Siemens–Elema AB, Jan. 1988.

* cited by examiner

Primary Examiner—Aaron J. Lewis
(74) Attorney, Agent, or Firm—Schiff Hardin & Waite

(57) ABSTRACT

A vaporizer for vaporizing a liquid anaesthetic has an inlet for a carrier gas, an outlet for the carrier gas and vaporized anaesthetic, a flow channel connecting the inlet to the outlet, a chamber for liquid anaesthetic, a first connection between the flow channel and the chamber, a second connection between the flow channel and the chamber downstream from the first connection and a throttle in the flow channel between the first connection and the second connection. The second connection has a conduit, one end of which is immersed in the liquid anaesthetic, and a valve connected to the other end of the conduit so as to increase safety, prevent leakage and erroneous dispensing and allow the use of liquid anaesthetics with a low boiling point. The valve is devised to open when there is a predetermined drop in pressure across the throttle, allowing liquid anaesthetic to be dispensed into the flow channel.

6 Claims, 1 Drawing Sheet

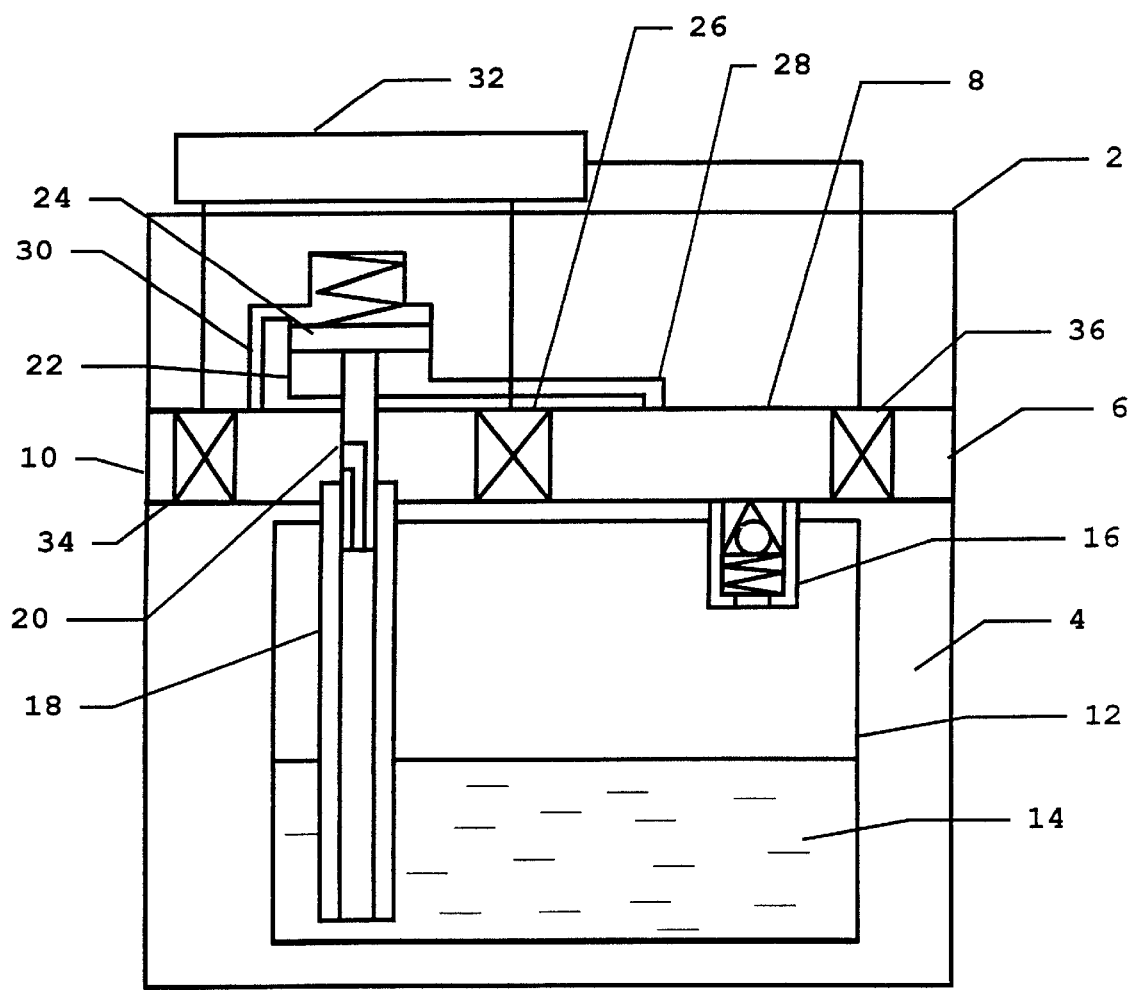

VAPORIZER

BACKGROUND OF THE INVENTION

1. Field of the Invention

The present invention is directed to a vaporizer, particularly for vaporizing a liquid anaesthetic, of the type having an inlet for a carrier gas, an outlet for the carrier gas and vaporized anaesthetic, a flow channel connecting the inlet and the outlet, a chamber for the liquid anaesthetic, a first connection between the flow channel and the chamber, a second connection between the flow channel and the chamber downstream from the first connection, and a throttle in the flow channel between the first and second connections.

2. Description of the Prior Art

The manual "Halothane Vaporizer 950, Enflurane Vaporizer 951, Isoflurane Vaporizer 952", Siemens-Elema AB, January 1988, contains a description of a vaporizer of the above general type. The vaporizer has a gas flow passage for a gas, a chamber for liquid anaesthetic and an adjustable throttle. An opening between the gas flow passage and the chamber is situated upstream from the adjustable throttle. A capillary tube with a nozzle in the gas flow passage and its other end immersed in the liquid anaesthetic in the chamber is arranged downstream from the adjustable throttle.

The presence of a gas flow generates a pressure drop across 20 the adjustable throttle. The higher pressure upstream from the throttle is propagated through the opening in the chamber and exerts pressure on the surface of the liquid, thereby forcing the liquid up through the capillary tube. The liquid is then injected through the nozzle into the gas flow passage and is vaporized.

The pressure drop across the throttle depends on the throttle's setting and controls the dispensing of liquid. Different concentrations of anaesthetic can be achieved by changing the throttle's setting.

The known vaporizer has an accuracy of ±0% of the value set. This is sufficient for all applications in conjunction with anaesthesia. However, this known vaporizer has certain disadvantages.

One disadvantage is that the vaporizer is not suitable for liquids with a boiling point close to the ambient temperature. Desflurane is one such liquid and has a boiling point of about 22° C. at normal atmospheric pressure.

Another disadvantage is that the vaporizer's operating pressure must first be reached each time a flow of gas is sent to the vaporizer for dispensing anaesthetic. This creates a small but measurable dispensing delay. Also, the chamber must first fill with gas before the pressure can act on the surface of the liquid. Moreover, a small amount of gas is lost when the chamber only contains a small amount of liquid. This subsequently has some effect on the concentration of dispensed anaesthetic.

Although these disadvantages only have a slight and virtually insignificant impact on vaporizer function, additional refinement of this function would still be desirable.

SUMMARY OF THE INVENTION

An object of the present invention is to provide a vaporizer which avoids the aforementioned problems.

The above object is achieved in accordance with the principles of the present invention in a vaporizer of the type initially described, wherein the second connection is formed as a conduit having one end immersed in the liquid anaesthetic, and a valve connected to the other end of the conduit, the valve being designed to open when a predetermined drop in pressure develops across the throttle, thereby allowing liquid anaesthetic to be dispensed into the flow channel.

The second connection between the chamber and the flow channel is devised with a conduit for liquid in the chamber and a valve which opens the conduit to the flow channel when the pressure drop across the throttle exceeds a preset value.

The conduit can be a capillary tube, as described above, but other conduits are possible. The conduit can be devised with a nozzle that atomizes the liquid when it is injected into the flow channel. This facilitates vaporization of the liquid.

The throttle can be adjustable in order to affect the drop in pressure, or the throttle can be fixed and an adjustable outlet valve can be arranged to regulate the drop in pressure.

The first connection can be open with most liquids, as in the prior art. Arranging a pre-biased check valve in the first connection, however, is advantageous for liquids with a low boiling point. In this manner, a higher pressure can be maintained in the chamber, thereby raising the boiling point. A pressure increase of 1 bar raises the boiling point of desflurane to about 28° C.

In the latter instance, the pressure drop must not be allowed to reach the opening pressure of the valve until the pressure in the flow channel exceeds the pressure in the chamber.

DESCRIPTION OF THE DRAWING

The single FIGURE is a schematic illustration of a vaporizer constructed and operating in accordance with the principles of the present invention.

DESCRIPTION OF THE PREFERRED EMBODIMENTS

The FIGURE shows one embodiment of the vaporizer according to the invention. The vaporizer 2 has a vaporizer housing 4 with an inlet 6 for a carrier gas, a flow channel 8 and an outlet 10. A chamber 12 holds a liquid anaesthetic 14, which is to be dispensed into the carrier gas in the flow channel 8.

The chamber 12 is connected to the flow channel 8 at two points. A pre-biased check valve 16 is arranged at the first point. In principle, the check valve 16 is only necessary for instances in which maintenance of a minimum positive pressure in the chamber 12 is desired in order to keep the liquid anaesthetic 14 from boiling. This applies primarily to the use of desflurane. The check valve 16 therefore can be excluded for other liquid anaesthetics 14.

At the second point, one end of a tube 18 is immersed in the liquid anaesthetic 14, and the other end of the tube 18 opens into the flow channel 8. A nozzle 20 is movably arranged at the other end of the tube 18. The nozzle 20 is part of the valve 22 for regulating when the dispensing of liquid anaesthetic 14 is to occur. The valve 22 has a spring-loaded disk 24 which ensures that the nozzle 20 is normally retracted into the tube 18, thereby preventing liquid anaesthetic 14 from flowing out into the flow channel 8.

A throttle 26 is arranged between the two points. The throttle 26 causes a pressure drop to develop in the flow channel 8. The valve 22 is connected, via a first channel 28, to the flow channel 8 upstream from the throttle 26 and connected, via a second channel 30, to the flow channel 8 downstream from the throttle 26. The first channel 28 and the second channel 30 are connected to the valve 22 so that the pressure drop across the throttle 26 has an opening effect on the valve. At a specific pressure drop, the nozzle 20 therefore is lifted up, out of the tube 18, thereby enabling liquid anaesthetic 14 to flow into the flow channel 8. The amount of liquid that flows out also depends on the pressure drop across the throttle 26.

The throttle 26 can be adjustable, so that the pressure drop can be regulated and, accordingly, the dispensing of liquid anaesthetic 14 also can be regulated.

The throttle 26 can be regulated by a control unit 32 with mechanical or electronic means.

Alternatively, the throttle 26 can be fixed and an adjustable outlet valve 34 can be used to regulate the drop in pressure. The outlet valve 34 can be mechanically or electronically adjustable by the control unit 32.

An inlet valve 36 also can be arranged in the flow channel 8 to further shield the vaporizer 2, thereby preventing any leakage or retrograde flows. The inlet valve can be a check valve, or can be regulated by the control unit 32.

Alternative embodiments of different details in the illustrated embodiment are possible. For example, the throttle 26 can be devised so a specific positive pressure is required on the inlet side to achieve the pre-set pressure drop. The valve 22 then can be arranged to open when the inlet pressure reaches this pressure. In other words, the second channel 30 then can be eliminated and spring loading can be adapted to the requisite inlet pressure.

Although modifications and changes may be suggested by those skilled in the art, it is the intention of the inventors to embody within the patent warranted hereon all changes and modifications as reasonably and properly come within the scope of their contribution to the art.

We claim as our invention:

1. A vaporizer for vaporizing a liquid anaesthetic, comprising:

an inlet for carrier gas;

an outlet for said carrier gas and vaporized anaesthetic;

a flow channel connecting said inlet to said outlet;

a chamber containing liquid anaesthetic;

a first connection between said flow channel and said chamber;

a second connection between said flow channel and said chamber downstream of said first connection;

a throttle disposed in said flow channel between said first connection and said second connection;

said second connection comprising a conduit having a first end immersed in said liquid anaesthetic in said chamber, and having a second end opposite to said first end; and a valve connected to said second end of said conduit, said valve opening when a predetermined drop in pressure occurs across said throttle to allow liquid anaesthetic to be dispensed from said chamber into said flow channel.

2. A vaporizer as claimed in claim 1 wherein said throttle comprises an adjustable throttle for controlling dispensing of said liquid anaesthetic.

3. A vaporizer as claimed in claim 1 wherein said throttle comprises a throttle with a fixed throughput, and said vaporizer further comprising an adjustable outlet valve disposed downstream of said second connection for controlling dispensing of said liquid anaesthetic.

4. A vaporizer as claimed in claim 1 wherein said valve comprises a nozzle for atomizing said liquid anaesthetic as said liquid anaesthetic is dispensed.

5. A vaporizer as claimed in claim 1 wherein said first connection comprises a pre-biased check valve.

6. A vaporizer as claimed in claim 5 wherein said check valve, said valve and said throttle operate in combination to prevent said valve from opening for dispensing liquid anaesthetic until a pressure in said flow channel is high enough to overcome the pre-biasing of said check valve to open said check valve.

* * * * *